(12) United States Patent
Pacetti et al.

(10) Patent No.: US 7,781,551 B2
(45) Date of Patent: Aug. 24, 2010

(54) ZWITTERIONIC COPOLYMERS, METHOD OF MAKING AND USE ON MEDICAL DEVICES

(75) Inventors: Stephen Pacetti, San Jose, CA (US); Wouter Roorda, Palo Alto, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/942,693

(22) Filed: Nov. 19, 2007

(65) Prior Publication Data

US 2008/0147178 A1    Jun. 19, 2008

Related U.S. Application Data

(60) Provisional application No. 60/866,800, filed on Nov. 21, 2006, provisional application No. 60/866,802, filed on Nov. 21, 2006, provisional application No. 60/866,804, filed on Nov. 21, 2006, provisional application No. 60/866,805, filed on Nov. 21, 2006, provisional application No. 60/866,798, filed on Nov. 21, 2006, provisional application No. 60/866,797, filed on Nov. 21, 2006, provisional application No. 60/866,796, filed on Nov. 21, 2006, provisional application No. 60/866,792, filed on Nov. 21, 2006.

(51) Int. Cl.
C08F 12/30 (2006.01)
C08F 12/26 (2006.01)
C08F 20/26 (2006.01)

(52) U.S. Cl. .................. 526/288; 526/274; 526/277; 526/310; 526/319; 526/320

(58) Field of Classification Search .......... 526/274, 526/277, 288, 310, 319, 320, 328.5, 329.6
See application file for complete search history.

(56) References Cited

U.S. PATENT DOCUMENTS

| | | | |
|---|---|---|---|
| 4,931,287 A | 6/1990 | Bae et al. |
| 5,019,096 A | 5/1991 | Fox, Jr. et al. |
| 5,163,952 A | 11/1992 | Froix |
| 5,258,020 A | 11/1993 | Froix |
| 5,607,467 A | 3/1997 | Froix |
| 5,616,338 A | 4/1997 | Fox, Jr. et al. |
| 5,674,242 A | 10/1997 | Phan et al. |
| 5,723,219 A | 3/1998 | Kolluri et al. |
| 5,824,049 A | 10/1998 | Ragheb et al. |
| 5,873,904 A | 2/1999 | Ragheb et al. |
| 5,879,713 A | 3/1999 | Roth et al. |
| 5,932,299 A | 8/1999 | Katoot |
| 5,962,138 A | 10/1999 | Kolluri et al. |
| 5,997,517 A | 12/1999 | Whitbourne |
| 6,096,070 A | 8/2000 | Ragheb et al. |
| 6,110,483 A | 8/2000 | Whitbourne et al. |
| 6,143,354 A | 11/2000 | Koulik et al. |
| 6,159,978 A | 12/2000 | Myers et al. |
| 6,180,632 B1 | 1/2001 | Myers et al. |
| 6,214,901 B1 | 4/2001 | Chudzik et al. |
| 6,245,760 B1 | 6/2001 | He et al. |
| 6,248,129 B1 | 6/2001 | Froix |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,299,604 B1 | 10/2001 | Ragheb et al. |
| 6,306,176 B1 | 10/2001 | Whitbourne |
| 6,344,035 B1 | 2/2002 | Chudzik et al. |
| 6,383,509 B1 | 5/2002 | Bates et al. |
| 6,387,379 B1 | 5/2002 | Goldberg et al. |
| 6,475,779 B2 | 11/2002 | Mathiowitz et al. |
| 6,482,834 B2 | 11/2002 | Spada et al. |
| 6,524,347 B1 | 2/2003 | Myers et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,613,432 B2 | 9/2003 | Zamora et al. |
| 6,620,617 B2 | 9/2003 | Mathiowitz et al. |
| 6,663,662 B2 | 12/2003 | Pacetti et al. |
| 6,730,064 B2 | 5/2004 | Ragheb et al. |
| 6,776,796 B2 | 8/2004 | Falotico et al. |
| 6,790,228 B2 | 9/2004 | Hossainy et al. |
| 6,890,583 B2 | 5/2005 | Chudzik et al. |
| 7,005,137 B1 | 2/2006 | Hossainy et al. |
| 7,008,667 B2 | 3/2006 | Chudzik et al. |
| 7,077,859 B2 | 7/2006 | Sirhan et al. |
| 7,094,256 B1 | 8/2006 | Shah et al. |
| 7,217,426 B1 | 5/2007 | Hossainy |
| 7,247,313 B2 | 7/2007 | Roorda et al. |
| 7,396,539 B1 | 7/2008 | Hossainy et al. |

(Continued)

OTHER PUBLICATIONS

U.S. Appl. No. 10/376,348, filed Feb. 26, 2003, Ding et al.
Kocakulak et al., "Investigation of Blood Compatibility of PMEA Coated Extracorporeal Circuits", J. of Bioactive and Compatible Polymers vol. 17, pp. 343-356 (2002).

*Primary Examiner*—Helen L Pezzuto
(74) *Attorney, Agent, or Firm*—Squire, Sanders & Dempsey, L.L.P.

(57) ABSTRACT

Biocompatible copolymers are manufactured to include a zwitterionic monomer and an alkoxy acrylate monomer. The alkoxy acrylate monomer can be a 2-methoxyethyl methacrylate (MOEMA) or 2-ethoxyethyl methacrylate (EOEMA). Alternatively, the alkoxy acrylate can be 2-methoxyethyl acrylate (MOEA) or 2-ethoxyethyl acrylate (EOEA). The alkoxy acrylate monomers advantageously give the zwitterionic copolymers greater ductility, strength, and toughness while maintaining a desired amount of hydrophilicity. The improved toughness allows the zwitterionic copolymers to be processed without cross-linking, which improves the elongation properties of the zwitterionic copolymer, and reduces the risk of cracking during use.

5 Claims, 3 Drawing Sheets

U.S. PATENT DOCUMENTS

| | | |
|---|---|---|
| 7,560,492 B1 | 7/2009 | Claude et al. |
| 7,563,454 B1 | 7/2009 | Pacetti |
| 2001/0007083 A1 | 7/2001 | Roorda |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083739 A1 | 5/2003 | Cafferata |

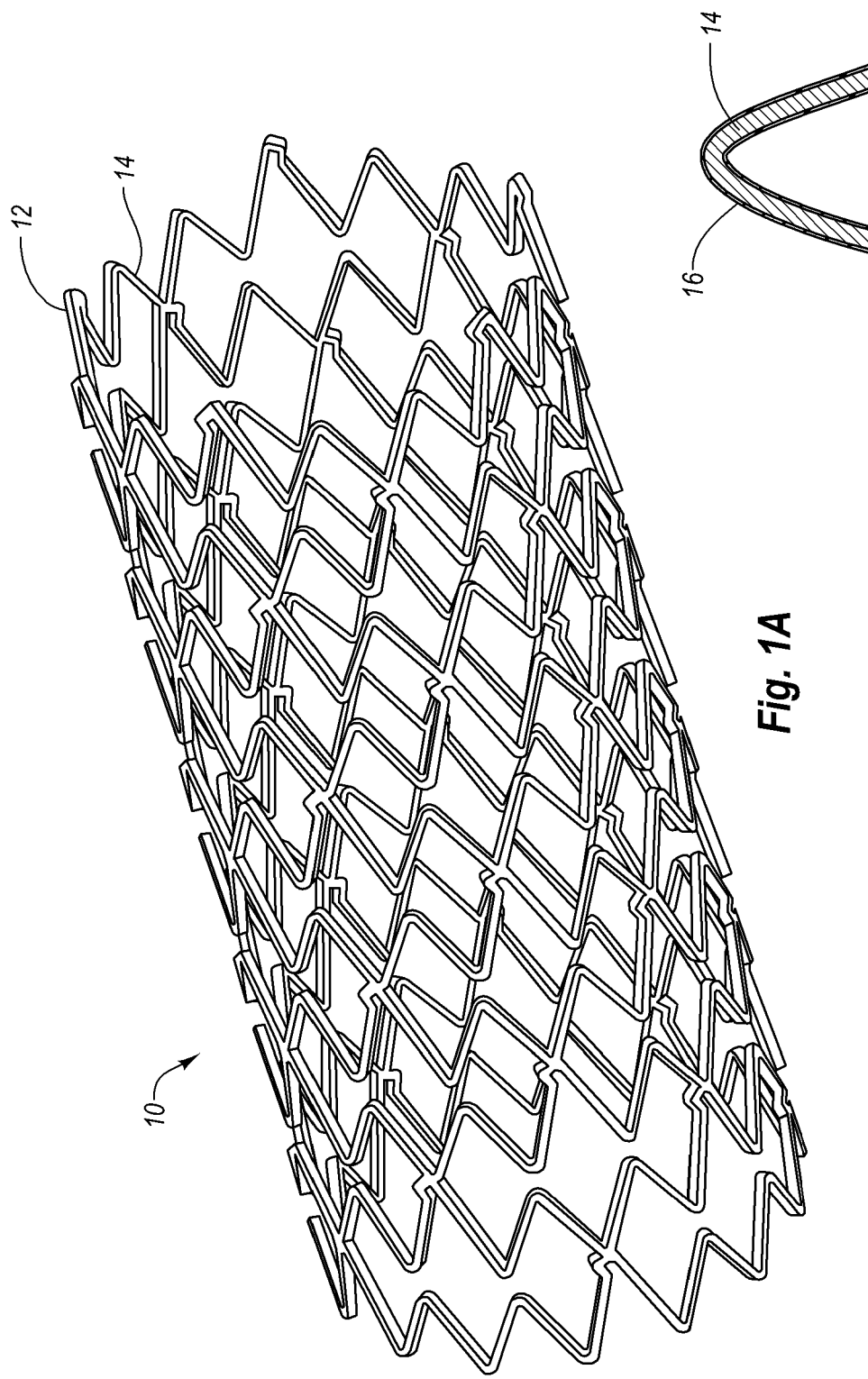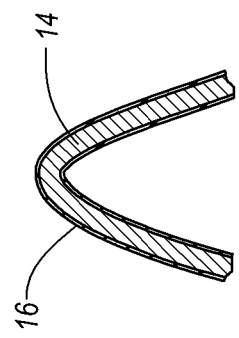

PMEA = poly(2-methyoxyethyl acrylate)

PHEA = poly(2-hydroxyethyl acrylate)

PEA = poly(ethyl acrylate)

PEHA = poly(2-ethylhexyl acrylate)

PPEA = poly(2-phenoxyethyl acrylate)

PHEMA = poly(2-hydroxyethyl methacrylate)

PMEA = poly(2-methyoxyethyl acrylate)

PHEA = poly(2-hydroxyethyl acrylate)

PEA = poly(ethyl acrylate)

PEHA = poly(2-ethylhexyl acrylate)

PPEA = poly(2-phenoxyethyl acrylate)

PHEMA = poly(2-hydroxyethyl methacrylate)

ZWITTERIONIC COPOLYMERS, METHOD OF MAKING AND USE ON MEDICAL DEVICES

CROSS-REFERENCE TO RELATED APPLICATIONS

This application claims the benefit of U.S. Provisional Patent Applications Nos. 60/866,800, 60/866,802, 60/866,804, 60/866,805 60/866,798, 60/866,797, 60/866,796, 60/866,792, all of which were filed on Nov. 21, 2006, and all of which are hereby incorporated by reference in their entirety. This application is related to co-pending U.S. patent application Ser. No. 11/942,695, entitled "Copolymers Having Zwitterionic Moieties and Dihydroxyphenyl Moieties and Medical Devices Coated with the Copolymers" co-pending U.S. patent application Ser. No. 11/942,704, entitled "Methods of Manufacturing Copolymers with Zwitterionic Moieties and Dihydroxyphenyl Moieties and Use of Same", co-pending U.S. patent application Ser. No. 11/942,705, entitled "Amino Acid Mimetic Copolymers and Medical Devices Coated with the Copolymers", co-pending U.S. patent application Ser. No. 11/942,969, entitled "Methods for Manufacturing Amino Acid Mimetic Copolymers and Use of Same" co-pending U.S. patent application Ser. No. 11/942,700, entitled "Copolymers Having 1-Methyl-2-Methoxyethyl Moieties", and co-pending U.S. patent application Ser. No. 11/942,707, entitled "Methods for Manufacturing Copolymers having 1-Methyl-2-Methoxyethyl Moieties and Use of Same", all of which were filed on Nov. 19, 2007, and all of which are hereby incorporated by reference in their entirety. Co-pending U.S. patent application Ser. No. 11/939,512, filed Nov. 13, 2007, and co-pending application Ser. No. 11/562,338, filed Nov. 21, 2006 are hereby incorporated by reference in their entirety.

BACKGROUND OF THE INVENTION

1. The Field of the Invention

Embodiments of the invention relate to zwitterionic copolymers. More particularly, embodiments of the invention relate to copolymers that include zwitterionic monomers and alkoxy acrylate monomers and methods of making and using the copolymers.

2. The Related Technology

Implantable medical devices, including stents, can be coated with polymers to give the implantable device beneficial properties when used in living tissue. Implant coatings, particularly stent coatings, typically need to simultaneously fulfill many criteria. Examples of desirable properties for implant coating properties include: adhesion to the implant (e.g. adhesion to stent struts) to prevent delamination; adequate elongation to accommodate implant deformation without buckling or cracking; sufficient hardness to withstand crimping operations without excessive damage; sterilizability; ability to control the release rate of a drug; biocompatibility including hemocompatibility and chronic vascular tissue compatibility; in the case of durable or permanent coatings, the polymer needs to be sufficiently biostable to avoid biocompatibility concerns; processability (e.g. production of stent coatings that are microns thick); reproducible and feasible polymer synthesis; and an adequately defined regulatory path.

Recently, polymers containing 2-(methacryloyloxyethyl)-2'-(trimethylammoniumethyl)phosphate ("phosphorylcholine" or "PC") monomers have been developed and used on implant devices. PC containing polymers have been shown to have many beneficial properties. For example, PC containing polymers are typically sterilizable, biocompatible, made from commercially available reagents, have received regulatory approval for certain embodiments, and provide a controlled drug release rate for higher molecular weight drugs.

However, PC coatings for use on implantable devices still need improvements with regard to several properties. Specifically, existing PC copolymers lack adequate elongation properties, especially when dry. Elongation properties are needed in order to accommodate implant deformation without coating buckling or cracking. Furthermore, PC copolymers need improvements in polymer hardness such that they can withstand crimping operations without excessive damage. Finally, some existing PC containing polymers have poorly controlled drug release rates for lower molecular weight drugs, including corticosteroids.

SUMMARY OF THE INVENTION

Embodiments of the invention relate to biocompatible copolymers that include zwitterion monomers, including but not limited to phosphorylcholine methacrylate monomers. In addition to the zwitterion monomer, the copolymers of the invention include an alkoxy acrylate monomer. The alkoxy acrylate monomer can be a 2-methoxyethyl methacrylate (MOEMA) or a 2-ethoxyethyl methacrylate (EOEMA). In an alternative embodiment, the alkoxy acrylate monomer can be 2-methoxyethyl acrylate (MOEA) or 2-ethoxyethyl acrylate (EOEA).

The alkoxy acrylate monomers advantageously give the zwitterionic copolymers greater ductility, strength, and toughness while maintaining a desired amount of hydrophilicity. The improved toughness allows the zwitterionic copolymers to be processed without cross-linking, which improves the elongation properties of the zwitterionic copolymer, and reduces the risk of cracking during use.

The zwitterionic copolymers can be manufactured by polymerizing a zwitterionic acrylate monomer and an alkoxy acrylate monomer in a polymerization reaction. The concentration of comonomers is selected to tune the hydrophilicity and glass transition temperature of the resulting thermoplastic polymer. The copolymers and terpolymers of the invention can be advantageously manufactured to have a desired glass transition temperature, when hydrated, to allow for good elongation and drug eluting properties.

These and other advantages and features of the invention will become more fully apparent from the following description and appended claims, or may be learned by the practice of the invention as set forth hereinafter.

BRIEF DESCRIPTION OF THE DRAWINGS

To further clarify the above and other advantages and features of the invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIG. 1A illustrates an example of a stent coated with a zwitterionic copolymer according to one embodiment of the invention; and FIG. 1B is a cross-section of a strut of the stent of FIG. 1A.

DETAILED DESCRIPTION OF EMBODIMENTS OF THE INVENTION

I. Zwitterionic Copolymer Structures

Figure 2:
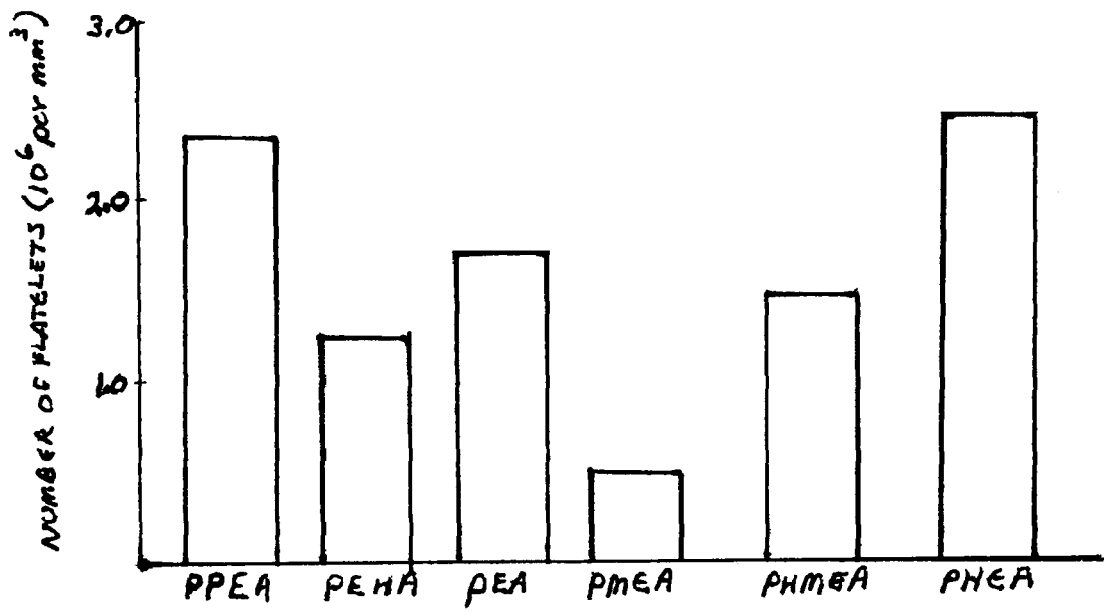
FIG. 2 is a graph showing the number of platelets adhered to onto the surface of several acrylate polymers of this invention.

The copolymers of the invention include a zwitterion monomer (e.g., phosphoryl choline methacrylate) and an alkoxy acrylate monomer (e.g., MOEMA). The zwitterionic monomers typically provide good biocompatibility properties and the alkoxy acrylate monomers typically provide polymer toughness without cross-linking. However the invention is not limited by these benefits.

In an embodiment of the invention, the zwitterionic copolymers incorporating the alkoxy acrylate monomer have the following chemical formula:

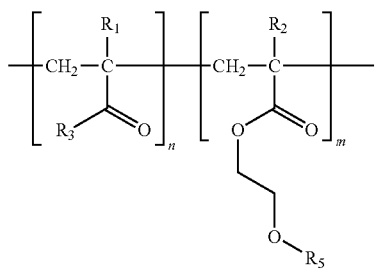

In the foregoing chemical formula, $R_1$ and $R_2$ are independently a hydrogen or methyl, $R_3$ is a zwitterionic group with a linker group of 2 to 12 carbons attached to the acryl or methacryl group via an ester or amide bond, $R_5$ is an ethyl or a methyl, n is in a range from about 0.01 to about 0.75, and m is in a range from about 0.25 to about 0.99. In an alternative embodiment, n is in a range from about 0.01 to about 0.25 and m is in a range from about 0.75 to about 0.99. In one embodiment, n+m=1. Unless otherwise stated, the monomers shown in the chemical formula above and other chemical formulas herein can be in any order within the copolymer molecule and the monomer linkages shown in the chemical formulas only represent that the monomers are part of the same copolymer molecule. Furthermore, unless otherwise stated, the polymeric molecules can include monomers other than those shown in the chemical formulas.

A. Zwitterion Monomers

The copolymers of the invention include a zwitterion group such as, but not limited to, phosphorylcholine (PC) monomer. Phosphorylcholine is a zwitterion that is analogous to the phospholipid molecules that form cell membranes in living organisms. Consequently, this molecule can be included in the copolymer of the invention for its biocompatibility. The zwitterion monomer also provides water absorption, which is useful for tuning the copolymers for desired drug permeability. In an embodiment, the zwitterion copolymer includes at least about 1.0 mol % to about 50 mol % of a zwitterion monomer.

Examples of suitable zwitterions include phosphorylcholine (which is also known as phosphatidyl choline and phosphocholine), phosphoryl ethanolamine, phosphatidyl ethanolamine, phosphoethanolamine, phosphatidyl serine, and sulfobetaine.

In one embodiment, the zwitterionic monomer includes a zwitterionic group with the following general formula.

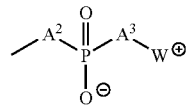

In the foregoing formula, the moieties $A^2$ and $A^3$, which are the same or different, are —O—, —S—, —NH— or a valence bond, and $W^+$ is a group comprising an ammonium, phosphonium or sulphonium cationic group and a group linking the anionic and cationic moieties which in one embodiment is a $C_{1-12}$-alkanediyl group. In another embodiment, the W+ is a $(CH)_2{}^+N(R^2)_3$, where $R^2$ are the same or different and each is hydrogen or $C_{1-4}$ alkyl, and m is from 1 to 4.

Alternatively, the zwitterionic group may be a betaine group (i.e., in which the cation is closer to the backbone), for instance a sulpho-, carboxy- or phosphor-betaine. In an embodiment, the betaine group has the formula -$A^4$-$R^3$—$N^+$ $(R^4)_2$—$R^5$—$V^-$, in which $A^4$ is a valence bond, —O—, —S—, or —NH—; V is a carboxylate, sulphonate or phosphate diester (monovalently charged) anion; $R^3$ is a valence bond (together with $A^4$) or alkanediyl, —C(O)alkylene- or —C(O)NH alkylene; the groups $R^4$ are the same or different and each is hydrogen or alkyl of 1 to 4 carbon atoms or the groups $R^4$ together with the nitrogen to which the are attached form a heterocyclic ring of 5 to 7 atoms; and $R^5$ is an alkanediyl of 1 to 20 carbon atoms, of 1 to 10 carbon atoms, or of 1 to 6 carbon atoms.

In yet another alternative embodiment, the zwitterionic group can be an amino acid moiety in which the alpha carbon atom (to which an amine group and the carboxylic acid group are attached) is joined through a linker group to the backbone of the copolymer. Such groups can be represented by the following general formula.

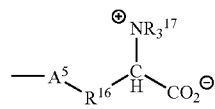

In the foregoing formula, $A^5$ is a valence bond, —O—, —S—, or —NH—; $R^{16}$ is a valence bond (optionally together with $A^5$) or alkanediyl, —C(O)alkylene- or —C(O)NH alkylene; the groups $R^{17}$ are the same or different and each is hydrogen or alkyl of 1 to 4 carbon atoms.

In yet another embodiment, the zwitterion-including monomer has the general formula YBX, wherein B is a straight or branched alkylene (alkanediyl), alkyleneoxaalkylene or alkylene oligo-oxaalkylene chain optionally including one or more fluorine atoms up to and including perfluorinated chains or, if X or Y include a terminal carbon atom bonded to B, a valence bond; X is a zwitterionic group; and Y is an ethylenically unsaturated polymerizable group.

B. Alkoxy Acrylate Monomers

The zwitterionic copolymers also include alkoxy acrylate monomers. For purposes of this invention, the term "acrylate monomer" includes methacrylates.

The alkoxy acrylate monomer can be 2-methoxyethyl methacrylate (MOEMA) 2-ethoxyethyl methacrylate (EOEMA), 2-methoxyethyl acrylate (MOEA), or 2-ethoxyethyl acrylate (EOEA).

The structures of MOEMA and EOEMA, are shown below.

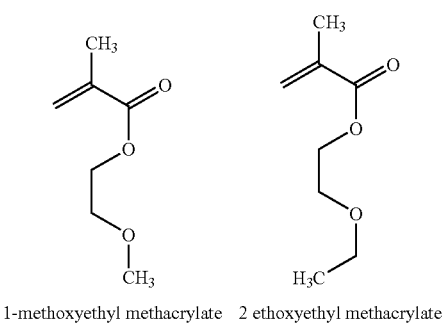

1-methoxyethyl methacrylate    2 ethoxyethyl methacrylate

These monomers can be incorporated into the zwitterionic copolymers of the invention to give the copolymer the desired ductility, strength, and toughness without requiring cross-linking. The MOEMA or EOEMA monomers provide the increased ductility, strength, and toughness necessary for forming a copolymer that is not cross-linked, while maintaining a suitable level of biocompatibility and drug permeability. Because the zwitterionic copolymers are not cross-linked they have improved elongation properties as compared to existing zwitterionic polymers, especially when dry.

One useful attribute of MOEMA and EOEMA is their effect on glass transition temperatures. The homopolymer of MOEMA has a glass transition temperature ($T_g$) of 16° C. (the $T_g$ for EOEMA is slightly lower). The glass transition temperatures of MOEMA and EOEMA are useful for designing copolymers with a glass transition temperature less than about 37° C. (i.e. body temperature) when hydrated.

Copolymers according to the invention that have a $T_g$ less than 37° C. are advantageous because they can be elastic at body temperature. In addition, the intermediate $T_g$ of MOEMA and EOEMA is desirable because it is sufficiently high so as to impart good mechanical strength to the PC copolymer at biological temperatures.

The $T_g$ of the dry polymer can also be tuned to within a desirable range. In one embodiment, the range is from about −30° C. to about 100° C. This range of dry $T_g$'s enables the coating to be adjusted to a temperature above the polymer $T_g$ in order to avoid coating damage during the deformation involved in crimping. It also allows a temperature to be used during the heat and pressure process used to deform a catheter balloon into the stent, which is above the $T_g$ of the catheter balloon.

Another benefit of the alkoxy acrylate monomers is their greater hydrophobicity compared to zwitterions. Consequently, the alkoxy acrylate monomers offset some of the hydrophilicity of the zwitterion monomer, thereby reducing water swelling. Controlling the degree of water swelling is necessary to avoid the need for cross-linking, to provide for a controlled release of medium to low molecular weight drugs and facilitates the manufacture of copolymers with desired elasticity.

As shown in the chemical structures of MOEMA and EOEMA, these monomers have an ether linkage in the alkoxy group. Although MOEMA and EOEMA are more hydrophobic than the zwitterion monomer, the ether linkage provides a degree of hydrophilicity. The ether linkage makes MOEMA and EOEMA more hydrophilic than alkyl methacrylates, for example. The intermediate hydrophilicity of MOEMA and EOEMA provides greater ability to incorporate the MOEMA or EOEMA into zwitterionic copolymers while properly controlling water swelling and thus drug permeability.

Another benefit of the MOEMA and EOEMA monomers is their anti-fouling properties. Considering the chemical structures of MOEMA and EOEMA, one can see that these compounds include the smallest PEG-type group possible: a single alkyloxyethyl group. PEG is known for its non-fouling and protein repelling properties. The analogous structure with PEG is the reason for the biocompatibility of MOEMA and EOEMA. The foregoing benefits can also be provided by MOEA and EOEA.

Figure 3:
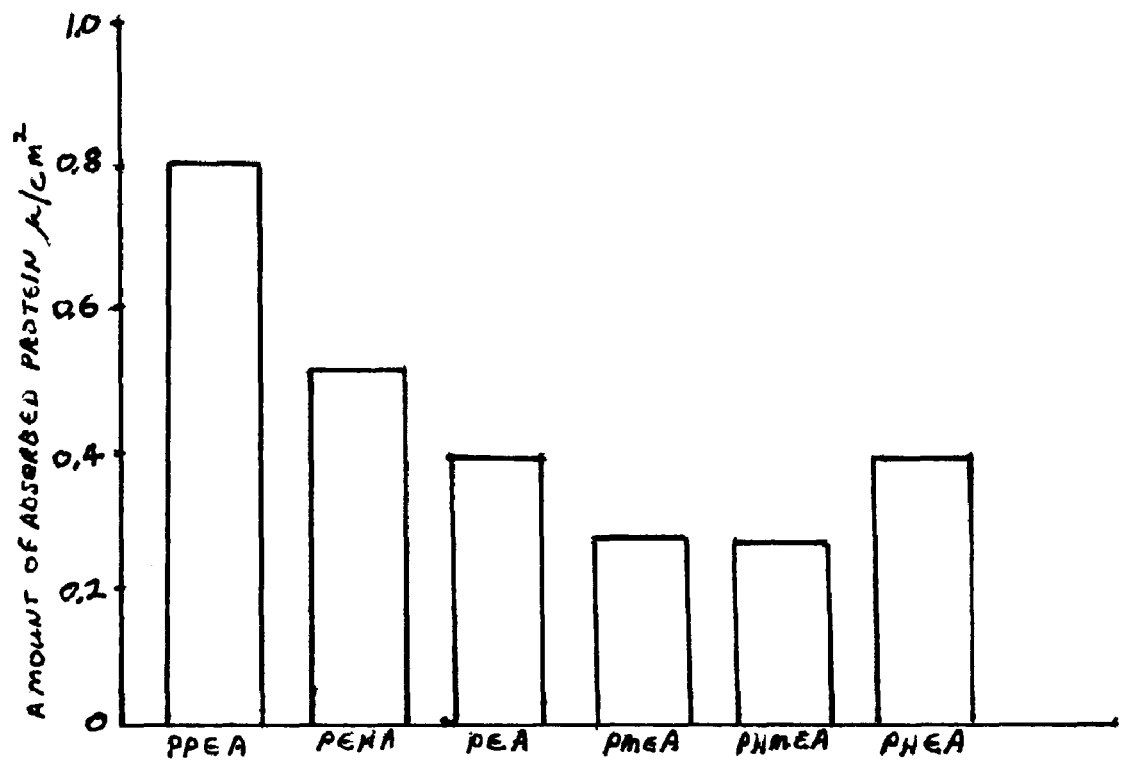
FIG. 3 is a graph of the amount of plasma protein adsorbed on the polymers of FIG. 2.

Studies on monomers analogous to the methoxy acrylate monomers of the invention illustrate the biocompatibility of the methoxy acrylate monomers in living tissue. For example, 2-methoxyethyl acrylate (MEA) has been extensively studied for blood contacting applications. Tanaka et al. compared the thrombogenicity of poly(2-methoxyethyl acrylate) (PMEA), poly(2-hydroxyethyl methacrylate) (PHEMA), poly(2-hydroxyethyl acrylate) (PHEA), and other alkyl methacrylates (Tanaka M., et al., Biomaterials 21 (2000) 1471-1481. Several measures of in vitro hemocompatibility, including human platelet adhesion, changes in platelet morphology, total absorbed protein from human plasma, amount of absorbed BSA, adsorbed human fibrinogens, and changes in protein conformation by circular dichroism were measured. In the graphs shown in FIG. 2 and FIG. 3 are data showing the number of platelets adhered and the total amount of plasma protein adsorbed onto the polymer in vitro.

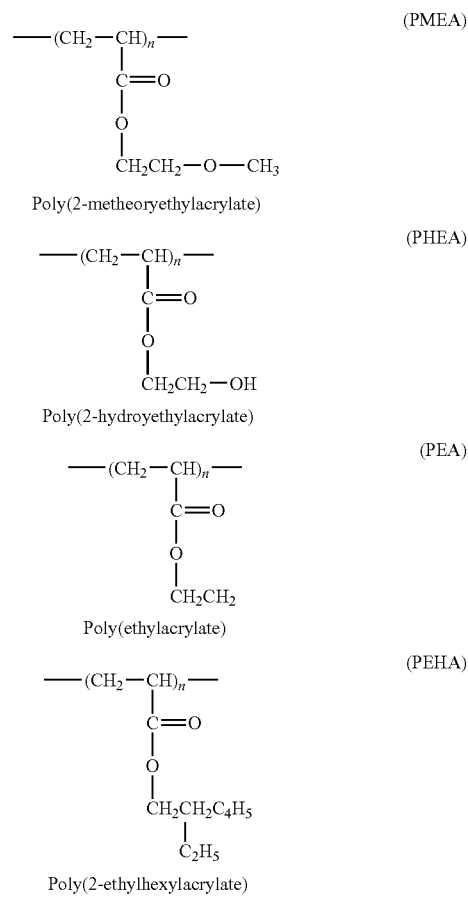

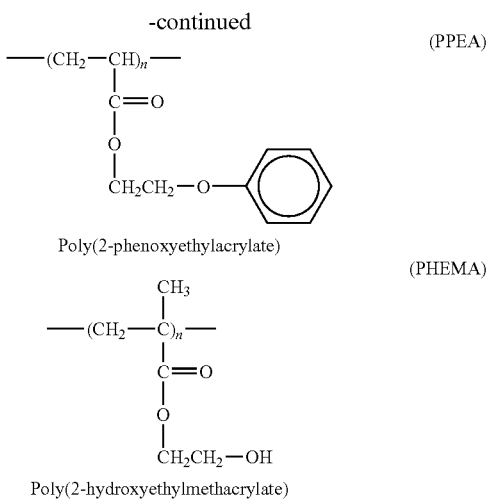

—(CH$_2$—CH)$_n$—
  |
  C=O
  |
  O
  |
  CH$_2$CH$_2$—O—⟨phenyl⟩

Poly(2-phenoxyethylacrylate) (PPEA)

—(CH$_2$—C(CH$_3$))$_n$—
  |
  C=O
  |
  O
  |
  CH$_2$CH$_2$—OH

Poly(2-hydroxyethylmethacrylate) (PHEMA)

As can be seen, the PMEA coating is the most hemocompatible of the polymers tested. Kocakular et al. investigated the blood compatibility of PMEA coated extracorporeal circuits (Kocakular M., et al., J Bioactive and Compatible Polymers Vol. 17, September 2002, p. 343). Hollow fiber oxygenators coated with PMEA were evaluated during twenty clinical procedures requiring cardiopulmonary bypass. The operations were compared to twenty operations with uncoated hollow fiber oxygenators. PMEA coatings were found to reduce both platelet adhesion and fibrinogen/albumin absorption. A coating of PEMA, known as the X Coating®, is used in the CAPIOX RX blood oxygenator sold by Terumo.

EOEMA is also known to be biocompatible as indicated by its use in contact lenses. The foregoing studies and uses support the conclusion that the zwitterionic copolymers that include MOEMA or EOEMA (or alternatively MOEA or EOEA), are biocompatible and suitable for use as drug eluting coatings for implant devices such as, but not limited to, stents.

II. Zwitterionic Terpolymers Including Alkyl Acrylates

In an alternative embodiment, the zwitterionic copolymer includes an alkyl acrylate co-monomer in addition to the alkoxy acrylate monomer and the zwitterion acrylate monomer. The combination of zwitterionic acrylate monomer, alkoxy acrylate monomer, and alkyl acrylate monomers allows for superior tunability in the mechanical and water swelling properties of the copolymers. An example of a chemical formula of a terpolymer according to one embodiment of the invention is as follows.

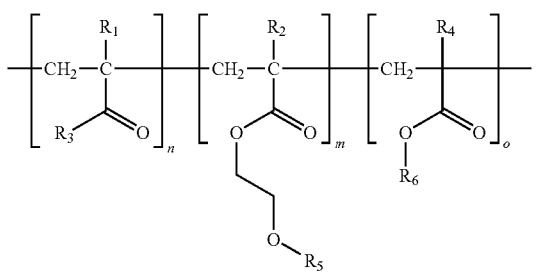

In the foregoing chemical formula, $R_1$, $R_2$, and $R_4$ are independently a hydrogen or methyl; $R_3$ is a zwitterionic group with a linker group of 2 to 12 carbons attached to the acryl or methacryl group via an ester or amide bond; $R_5$ is a ethyl or methyl; $R_6$ is a straight chain, branched, unsaturated or cyclic hydrocarbon of one to sixteen carbon atoms; n is in a range from about 0.01 to about 0.75; m is in a range from about 0.1 to about 0.99; o is in a range from about 0.1 to about 0.99; and m+n+o=1.

Examples of suitable groups for $R_6$ include, but are not limited to, methyl, ethyl, n-propyl, isopropyl, n-butyl, isobutyl, sec-butyl, 2-ethyl-hexyl, n-hexyl, cyclohexyl, n-hexyl, isobornyl, and trimethylcyclohexyl groups.

In one embodiment, the alkyl acrylate monomer is n-butyl methacrylate, which, in its homopolymer form, is referred to as poly(n-butyl methacrylate) (PBMA). The PBMA homopolymer is an amorphous, thermoplastic polymer that possesses many properties desired for an implant device coating and particularly stent coatings. PBMA has a $T_g$ in the range of 20-25° C. (depending on molecular weight) (J. Brandrup, E. H. Immergut, E. A. Grulke "Polymer Handbook," 4th Edition, John Wiley & Sons, 1999). PBMA is also has a combination of a non-polar butyl tail, a polar ester group, and some limited hydrogen bonding ability via the carbonyl oxygen. This combination of a low $T_g$ and different chemical moieties allows for optimization of its non-covalent adhesive interactions. PBMA adheres well to metal surfaces and is very biostable as it has an all carbon backbone consisting of alternating secondary and quaternary carbons. Ester groups can be hydrolyzed, but the ester group of PBMA is alpha to a tertiary carbon that makes the carbonyl carbon sterically hindered such that hydrolysis of the ester is difficult. PBMA is also known to be biocompatible with respect to vascular tissue and hemocompatibility.

With regard to mechanical integrity, PBMA can have good elongation due to its $T_g$ below body temperature. PBMA is quite hydrophobic, with water absorption of only 0.4% (T. R, Aslamazova. et al., Polymer Science, USSR, Vol. 25. No. 6, pp. 1484-1490, 1933). Terpolymers including a zwitterionic monomer, an alkoxy acrylate monomer, and PBMA can possess desired water swelling, mechanical strength, and elongation, without cross-linking.

III. Methods of Manufacturing

The method of manufacturing the copolymers of the invention includes reacting a zwitterionic acrylate monomer with an alkoxy acrylate monomer. The copolymers can be synthesized using free radical polymerization, atom transfer radical polymerization, cationic polymerization, anionic polymerization, iniferter polymerization, or other suitable reactions.

Free radical polymerization is carried out in a solvent using an initiator. Examples of solvents suitable for carrying out the polymerization reaction include alcoholic solvents such as, but not limited to, methanol, ethanol, and isopropanol. Examples of suitable initiators for carrying out the polymerization reaction include peroxides, such as, but not limited to, benzoyl peroxide, and azo compounds. A specific example of a suitable initiator is 2,2'-azo-bis(2-methylpropionitrile). Those skilled in the art are familiar with the conditions for carrying out the foregoing polymerization reactions and other similar polymerization reactions suitable for yielding the copolymers of the invention.

An alternate path to synthesizing the zwitterionic copolymers includes copolymerizing one or more monomers to form an intermediate polymer and coupling the alkoxy group and/or the zwitterion group to the intermediate polymer. In one embodiment, the intermediate polymer can be synthesized from an acrylic acid monomer or a methacrylic acid monomer and optionally the zwitterion acrylate monomer, the alkoxy acrylate monomer, and/or the alkyl acrylate monomer. The acrylic acid or methacrylic acid monomers provide carboxyl groups in the intermediate polymer where the zwitterion group, alkoxy group, or alkyl group can be coupled.

Polymerization of the monomers to form the intermediate polymer can be carried out using the polymerization techniques described above. Several coupling chemistries are suitable for coupling a hydroxyl or amino functional zwitterionic group, a hydroxyl functional alkoxy group, or a hydroxyalkyl group to the intermediate polymer, including, but not limited to, conversion to the acid chloride or use of carbodiimides. A particularly facile technique uses dicyclohexyl carbodiimide (DCC) and 4-(dimethylamino)pyridinium (DPTS) as described in M. Trollsas, J. Hedrick, Macromolecules 1998, 31, 4390-4395.

Yet another technique for synthesizing the copolymers begins with the homopolymer of the alkoxy acrylate monomer. The alkoxy groups of this homopolymer can be exchanged off by catalytic esterification to form a bond between a zwitterion compound and the intermediate homopolymer. An example of a suitable catalyst for esterification is an organic acid catalyst, such as, but not limited to, p-toluene sulfonic acid.

In another alternative embodiment, the zwitterion acrylate monomer can be used to synthesize an intermediate homopolymer. The alkoxy group can then be coupled to an intermediate zwitterion homopolymer using transesterification.

The zwitterionic terpolymers of the invention can also be manufactured using any of the foregoing alternative synthesis routes.

The zwitterionic polymers can be made mechanically robust by increasing the polymer's number average molecular weight. The molecular weight of the polymer can be increased, if desired, so long as processability is not compromised. In one embodiment, the molecular weight of the polymer is in a range from about 20K to 800K. In an alternative embodiment, the molecular weight can be in a range from 100K to 600K. If a tacky or adhesive polymer is desired the molecular weight can be in a range from about 2K to about 200K. A high molecular weight yields a higher ultimate elongation for the polymer, which typically improves coating integrity. For a thermoplastic polymer, high molecular weight typically yields better mechanical properties.

In one embodiment, the polymer compositions are manufactured to have a desired $T_g$ when hydrated. The $T_g$ of the polymer can be calculated by knowing the amount of water absorbed and the $T_g$s derived from measurements of the homopolymer of the respective monomers. In an embodiment, the $T_g$ is calculated using the Fox equation, which is shown below.

$$\frac{1}{T_g^{Polymer}} = \frac{W^{PC}}{T_g^{PC}} + \frac{W^{Water}}{T_g^{Water}} + \frac{W^{Methacrylate}}{T_g^{Methacrylate}}$$

where:
$T_g$=Glass transition temperature of the homopolymer or pure material.
$T_g^{water}$=40° C.
W=Weight fraction of the components.

Once the water absorption of the polymer is known, which is usually measured experimentally, the copolymer $T_g$ can be estimated with the desired target. In one embodiment the desired target $T_g$ is in a range from about −30° C. to about 37° C. when in the fully hydrated state. In another range, the $T_g$ is between about 0° C. and about 37° C. when hydrated. With a $T_g$ of less than 37° C., the copolymers of the invention will have a high degree of polymer mobility when placed in vivo. This feature allows the surface of the polymer to enrich in hydrophilic monomer content, which is advantageous for biocompatibility.

In an alternative embodiment, the co-polymer is designed to have a desired $T_g$ for the polymer in the dry state. In an embodiment, the $T_g$ of the polymer when dry is in a range from about −30° C. to about 100° C. or in an alternative range from 0° C. to about 70° C.

The biocompatibility of commercially available PC including polymers has been attributed to a high mol % of PC (e.g. 23 mol % PC content for commercially available PC1036). With a design $T_g$ of less than 37° C. for the zwitterionic polymers of the invention, the polymer will have a high degree of polymer mobility when placed in vivo. This feature of the invention allows the surface of the polymer to enrich in zwitterion content, ensuring the biocompatibility of the copolymers across a wide range of zwitterion content (e.g., 1 mol %-50 mol %).

Terpolymers of a zwitterion monomer, an alkoxy acrylate monomer and an alkyl acrylate monomer can be manufactured using the same techniques as above, with the addition of a polymerizable monomer of an alkyl acrylate monomer. Examples of suitable alkyl acrylate monomers include ethyl methacrylate, n-butyl methacrylate, lauryl methacrylate, methyl methacrylate, isopropyl methacrylate, n-propyl methacrylate, isobutyl methacrylate, sec-butyl methacrylate, tert-butyl methacrylate, n-hexyl methacrylate, cyclohexyl methacrylate, 2-ethylhexyl methacrylate, phenyl methacrylate, benzyl methacrylate, isobornyl methacrylate, trimethylcyclohexyl methacrylate, n-dodecyl methacrylate, methacrylates with pendant groups comprising up to 16 carbons, methyl acrylate, ethyl acrylate, propyl acrylate, n-butyl acrylate, isobutyl acrylate, sec-butyl acrylate, n-hexyl acrylate, cyclohexyl acrylate, phenyl acrylate, benzyl acrylate, styrene, alkyl substituted styrene, ethylene, propylene, 1-butene, and isobutylene.

IV. Use of Coatings on Implantable Devices

The foregoing novel polymers are suitable for use on any implantable medical device that is compatible with zwitterion-including polymers. The copolymers can be used alone as a coating or can be combined with other polymers or agents to form a polymer coating. For example, the polymers may be blended with poly(vinyl pyrrolidinone), poly(n-butyl methacrylate), poly(n-butyl methacrylate) copolymers, methacrylate polymers, acrylate polymers, and/or a terpolymers of hexyl methacrylate, vinyl acetate, and vinyl pyrrolidinone.

The polymer coatings can be applied to a medical device using any techniques known to those skilled in the art or those that may be developed for applying a coating to a medical device. Examples of suitable techniques for applying the coating to the medical device include spraying, dip coating, roll coating, spin coating, powder coating, and direct application by brush or needle. One skilled in the art would appreciate the many different techniques used in powder coating and apply them to the embodiments of the invention. The copolymers can be applied directly to the surface of the implant device, or they can be applied over a primer or other coating material.

In one embodiment, the polymer coatings are applied to a medical device using a solvent-based technique. The polymer can be dissolved in the solvent to form a solution, which can be more easily applied to the medical device using one or more of the above mentioned techniques or another technique. Thereafter substantially all or a portion of the solvent can be removed to yield the polymer coating on a surface of the medical device.

Examples of suitable solvents that can be used with the copolymers of the invention include, but are not limited to, dimethylacetamide (DMAC), dimethylformamide (DMF), tetrahydrofuran (TWF), dimethylsulfoxide (DMSO), cyclohexanone, xylene, toluene, acetone, n-butanol, i-propanol, methyl ethyl ketone, propylene glycol monomethyl ether, methyl t-butyl ketone, methyl isobutyl ketone, ethyl acetate, n-butyl acetate, ethanol, methanol, chloroform, trichloroethylene, 1,1,1-trichloreoethane, methylene chloride, cyclohexane, octane, n-hexane, pentane, and dioxane. Solvent mixtures can be used as well. Representative examples of the mixtures include, but are not limited to, DMAC and methanol (50:50 w/w); water, i-propanol, and DMAC (10:3:87 w/w); and i-propanol and DMAC (80:20, 50:50, or 20:80 w/w).

Examples of suitable implantable devices that can be coated with the copolymers of the invention include coronary stents, peripheral stents, catheters, arterio-venous grafts, bypass grafts, pacemaker and defibrillator leads, anastomotic clips, arterial closure devices, patent foramen ovale closure devices, and drug delivery balloons. The copolymers are particularly suitable for permanently implanted medical devices.

The implantable device can be made of any suitable biocompatible materials, including biostable and bioabsorbable materials. Suitable biocompatible metallic materials include, but are not limited to, stainless steel, tantalum, titanium alloys (including nitinol), and cobalt alloys (including cobalt-chromium-nickel and cobalt-chromium-tungsten alloys). Suitable nonmetallic biocompatible materials include, but are not limited to, polyamides, fluoropolymers, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and the like, and combinations of these).

The copolymers are particularly advantageous as a coating for stents due to their elongation properties, which allows the coated stent to be crimped and expanded without cracking the coating. The stents can be composed of wire structures, flat perforated structures that are subsequently rolled to form tubular structures, or cylindrical structures that are woven, wrapped, drilled, etched or cut.

FIG. 1A shows an example stent 10 coated with a polymer including zwitterionic monomers and alkyl acrylate monomers. Stent 10 includes a generally tubular body 12 with a lumen. The struts of body 12 (e.g. strut 14) provide a supporting structure for coating the polymers of the invention.

FIG. 1B illustrates a cross-section of the stent of FIG. 1A coated with a polymer coating 16 according to an embodiment of the invention. The polymer coating 16 can be conformal as in FIG. 1B. Alternatively, the coating can be ablumenal, luminal, or any combination thereof. In one embodiment, the copolymers of the invention are elastic at body temperatures and can therefore expand without cracking as the stent expands during use.

The polymer coated stents of embodiments of the invention can be self-expanding or balloon expandable. The copolymer coatings of the invention can be particularly advantageous for self expanding stents. Self expanding stents are typically restrained by a sheath that is removed during deployment of the stent. The copolymers of the invention have improved mechanical strength to better withstand the friction exerted on the polymer as the sheath is removed.

In one embodiment, a bioactive agent is associated with the coated medical devices of the invention. The bioactive agent can be incorporated into a base coat, top coat, mixed with the novel copolymers of the invention, and/or incorporated or otherwise applied to a supporting structure of the medical device.

The bioactive agent can have any therapeutic effect. Examples of suitable therapeutic properties include anti-proliferative, anti-inflammatory, antineoplastic, antiplatelet, anti-coagulant, anti-fibrin, antithrombonic, antimitotic, antibiotic, antiallergic and antioxidant properties.

Examples of suitable bioactive agents include synthetic inorganic and organic compounds, proteins and peptides, polysaccharides and other sugars, lipids, DNA and RNA nucleic acid sequences, antisense oligonucleotides, antibodies, receptor ligands, enzymes, adhesion peptides, blood clot agents, including streptokinase and tissue plasminogen activator, antigens, hormones, growth factors, ribozymes, retroviral vectors, anti-proliferative agents including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), 40-epi-(N-1-tetrazolyl)-rapamycin, 40-O-[2-(2-hydroxy)ethoxy]ethyl-rapamycin, Biolimus A9 (biosensors International, Singapore), deforolimus, AP23572 (Ariad Pharmaceuticals), paclitaxel, docetaxel, methotrexate, azathioprine, vincristine, vinblastine, fluorouracil, doxorubicin hydrochloride, mitomycin, antiplatelet compounds, anticoagulants, antifibrin, antithrombins including sodium heparin, low molecular weight heparins, heparinoids, hirudin, argatroban, forskolin, vapiprost, prostacyclin, prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors including Angiomax ä, calcium channel blockers including nifedipine, colchicine, fibroblast growth factor (FGF) antagonists, fish oil (omega 3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements including vitamins, anti-inflammatory agents including aspirin, tacrolimus, dexamethasone, dexamethasone acetate, dexmethasone phosphate, momentasone, cortisone, cortisone acetate, hydrocortisone, prednisone, prednisone acetate, betamethasone, betamethasone acetate, clobetasol, cytostatic substances including angiopeptin, angiotensin converting enzyme inhibitors including captopril, cilazapril or lisinopril, antiallergic agents is permirolast potassium, alpha-interferon, bioactive RGD, and genetically engineered epithelial cells. Other bioactive agents which are currently available or that may be developed in the future for use with DESs may likewise be used and all are within the scope of this invention.

The medical devices of the invention can be used in any vascular, tubular, or non-vascular structure in the body. In an embodiment, a coated stent can be used in, but is not limited to use in, neurological, carotid, coronary, aorta, renal, biliary, ureter, iliac, femoral, and popliteal vessels.

IV. EXAMPLES

The following are specific examples of copolymers of zwitterionic monomers and alkyl acrylate monomers. The following copolymers are useful for coating implantable medical devices.

Example 1

Example 1 describes a copolymer of methacryloyloxyethyl phosphoryl choline and 2-methoxyethyl methacrylate.

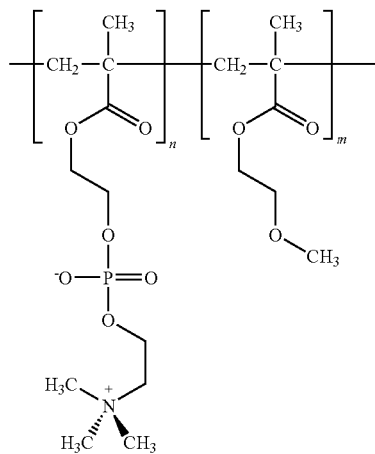

in which, n is in a range from about 0.01 to about 0.5; and m is in the range from about 0.5 to about 0.99

Example 2

Example 2 describes a copolymer of methacryloyloxyethyl phosphoryl choline, 2-ethoxyethyl methacrylate, and n-butyl methacrylate.

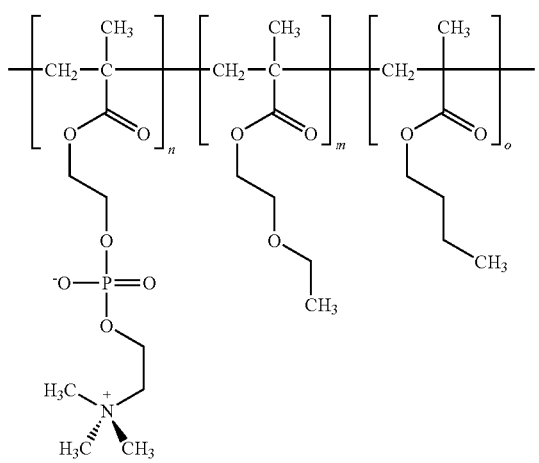

in which, n is in the range from about 0.01 to about 0.5;

m is in the range from about 0.01 to about 0.5; and o is in the range from about 0.01 to about 0.98.

Example 3

Example 3 describes a method for manufacturing a stent using the polymers of Examples 1 and/or 2. In a first step, a primer coating is applied to the stent. A primer solution including between about 0.1 mass % and about 15 mass %, (e.g., about 2.0 mass %) of poly(n-butyl methacrylate) (PBMA) and the balance, a solvent mixture of acetone and cyclohexanone (having about 70 mass % of acetone and about 30 mass % of cyclohexanone) is prepared. The solution is applied onto a stent to form a primer layer.

To apply the primer layer, a spray apparatus, (e.g., Sono-Tek MicroMist spray nozzle, manufactured by Sono-Tek Corporation of Milton, N.Y.) is used. The spray apparatus is an ultrasonic atomizer with a gas entrainment stream. A syringe pump is used to supply the coating solution to the nozzle. The composition is atomized by ultrasonic energy and applied to the stent surfaces. A useful nozzle to stent distance is about 20 mm to about 40 mm at an ultrasonic power of about one watt to about two watts. During the process of applying the composition, the stent is optionally rotated about its longitudinal axis, at a speed of 100 to about 600 rpm, for example, about 400 rpm. The stent is also linearly moved along the same axis during the application.

The primer solution is applied to a 15 mm Triplex, N stent (available from Abbott Vascular Corporation) in a series of 20-second passes, to deposit, for example, 20 μg of coating per spray pass. Between the spray passes, the stent is allowed to dry for about 10 seconds to about 30 seconds at ambient temperature. Four spray passes can be applied, followed by baking the primer layer at about 80° C. for about 1 hour. As a result, a primer layer can be formed having a solids content of about 80 μg. For purposes of this invention, "Solids" means the amount of the dry residue deposited on the stent after all volatile organic compounds (e.g., the solvent) have been removed.

In a subsequent step, a copolymer solution is prepared. The copolymer solution includes the copolymer of Examples 1 and/or Example 2. The solution is prepared by dissolving between about 0.1 mass % and about 15 mass %, (e.g., about 2.0 mass %) of the copolymer in a solvent. The solvent can be a mixture of about 50 mass % ethanol and about 50 mass % n-butanol.

In a manner similar to the application of the primer layer, the copolymer solution is applied to a stent. Twenty spray passes are performed with a coating application of 10 μg per pass, with a drying time between passes of 10 seconds, followed by baking the copolymer layer at about 60° C. for about 1 hour, to form a layer having a solids content between about 30 μg and 750 μg, (e.g., about 225 μg).

Example 4

Example 4 describes a method for manufacturing a drug eluting stent according to an embodiment of the invention. The medical device is manufactured using the same method as in Example 3, except that instead of the copolymer solution, a polymer-therapeutic solution is prepared and applied using the following formula.

A drug-including formulation is prepared that includes:

(a) between about 0.1 mass % and about 15 mass %, (e.g., about 2.0 mass %) of the copolymer of Example 1 and/or Example 2;

(b) between about 0.1 mass % and about 2 mass %, for example, about 1.0 mass % of bioactive agent. In one embodiment, the bioactive agent is ABT-578 (available from Abbott Vascular Corp. of Chicago, Ill.); and (c) the balance, a solvent mixture including about 50 mass % of ethanol and about 50 mass % of n-butanol.

The drug-including formulation is applied to the stent in a manner similar to the application of the copolymer solution in Example 3. The process results in the formation of a drug-polymer reservoir layer having a solids content between about 30 μg and 750 μg, (e.g., about 225 μg), and a drug content of between about 10 μg and about 250 μg, (e.g., about 75 μg).

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Recitation of ranges of values herein are merely intended to serve as a shorthand method of referring individually to each separate value falling within the range, unless otherwise indicated herein, and each separate value is incorporated into the specification as if it were individually recited herein.

What is claimed is:

1. A biocompatible polymer of the chemical formula:

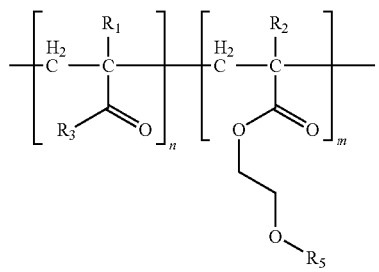

in which, $R_1$ and $R_2$ are independently a hydrogen or methyl;

$R_3$ is a zwitterion group having the formula:

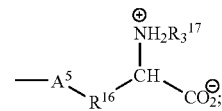

in which $A^5$ is selected from the group consisting of —O—, —S— and —NH—;

$R^{16}$ is selected from the group consisting of alkanediyl, —C(O)alkylene- and —C(O)NHalkylene-;

the $R_3{}^{17}$ groups are independently selected from the group consisting of hydrogen, 1 to 4 carbon atoms or, taken together with the nitrogen to which they are bonded, a heterocyclic ring of 5 to 7 atoms;

$R_5$ is an ethyl or methyl;

n is in an range from about 0.01 to about 0.75; and m is in a range from about 0.25 to about 0.99.

2. A biocompatible polymer as in claim 1, in which $R_5$ is a methyl.

3. A biocompatible polymer as in claim 1, in which $R_5$ is an ethyl.

4. The biocompatible polymer of claim 1, wherein $R_3$ is selected from the group consisting of phosphorylcholine, phosphorylethanolamine, phosphatidylethanolamine, phosphatidylserine, sulfobetaine and combinations thereof.

5. The biocompatible polymer of claim 1, wherein the copolymer has a number average molecular weight of about 20 kD to about 800 kD.

* * * * *